(12) United States Patent
Botella et al.

(10) Patent No.: US 6,194,639 B1
(45) Date of Patent: *Feb. 27, 2001

(54) ACC SYNTHASE GENES FROM PINEAPPLE

(75) Inventors: José Botella, Kenmore; Garth Sanewski, Nambour, both of (AU)

(73) Assignees: The University of Queensland; Golden Circle Limited; The State of Queensland, all of Queensland (AU)

(*) Notice: Subject to any disclaimer, the term of this patent is extended or adjusted under 35 U.S.C. 154(b) by 30 days.

This patent is subject to a terminal disclaimer.

(21) Appl. No.: 08/846,826

(22) Filed: May 1, 1997

(30) Foreign Application Priority Data

May 1, 1996 (AU) .................................................. PN 9582

(51) Int. Cl.[7] .............................. A01H 5/00; A01H 5/08; C07H 21/04; C12N 15/82

(52) U.S. Cl. ...................... 800/298; 435/320.1; 536/23.2; 536/23.6; 800/283; 800/286

(58) Field of Search .................................. 536/23.6, 23.2; 435/172.3, 320.1; 800/205, 283, 286, 298

(56) References Cited

FOREIGN PATENT DOCUMENTS

WO 92/04456 3/1992 (WO).

OTHER PUBLICATIONS

Botella et al., "Identification and characterization of a full-length cDNA encoding for an auxin–induced 1–aminocyclopropane–1–carboxylate synthase from indolated mung bean hypocotyl segments and expression of its mRNA in response to indole–3–acetic acid," *Plant Molecular Biology*, 20:425–436 (1992).

Miki et al., "Nucleotide Sequence of a cDNA for 1–Aminocyclopropane–1–Carboxylate Synthase from Melon Fruits," *Plant Physiol.*, 107:297–298 (1995).

Theologis, "One Rotten Apple Spoils the Whole Bushel: The Role of Ethylene in Fruit Ripening," *Cell*, 70:181–184 (Jul. 24, 1992).

Kende, "Ethylene Biosynthesis, "*Annu. Rev. Plant Physiol. Plant Mol. Biol.*, 44:283–307 (1993).

Olson et al., "Differential expression of two genes for 1–aminocycloprane–1–carboxylate synthase in tomato fruits," *Proc. Natl. Acad. Sci. USA*, 88:5340–5344 (Jun. 1991).

Rottmann et al., "1–Aminocyclopropane–1–Carboxylate Synthase in Tomato is Encoded by a Multigene Family Whose Transcription is Induced During Fruit and Floral Senescence," *J. Miol. Biol.*, 222:937–961 (19910.

Yip et al., "Differential accumulation of transcripts for four tomato 1–aminocycloprane–1–carboxylate synthase homologs under various conditions," *Proc. Natl. Acad. Sci. USA*, 89:2475–2479 (Mar. 1992).

Van Der Straeten et al., "Cloning, genetic mapping, and expression analysis of an *Arabidopsis thaliana* gene that encodes 1–aminocyclopropane–1–carboxylate synthase," *Proc. Natl. Acad. Sci. USA*, 89:9969–9973 (Oct. 1992).

Van der Straeten et al. Cloning and sequence of two different cDNAs encoding 1–aminocyclopropane–1–carboxylate synthase in tomato. PNAS USA. 87:4859–4863, Jun. 1990.*

Nakajima et al. Molecular cloning and sequence of a complementary DNA encoding 1–aminocyclopropane–1–carboxylate synthase induced by tissue wounding. Plant Cell Physiology. 31(7):1021–1029, Sep. 1990.*

Sato et al. The 1–aminocyclopropane–1–carboxylate synthase of Cucurbita. The Journal of Biological Chemistry. 266(6):3752–3759, Feb. 1992.*

Botella et al. Identification and characterization of a full-length cDNA encoding for an auxin–induced 1–aminocyclopropane–1–carboxylate synthase from etiolated mung bean hypocotyl segments and expressions of its mRNA response to indole–3–acetic acid. Pl, Nov, 1992.*

Liang et al. The 1–aminocyclopropane–1–carboxylate synthase gene family of *Arabidopsis thaliana*. PNAS USA. 89:11046–11050, Nov. 1992.*

Bailey et al. Nucleotide sequence of the *Nicotiana tabacum* cv Xanthi gene encoding 1–aminocyclopropane– 1–carboxylate synthase. Plant Physiology. 100:1615–1616, Nov. 1992.*

Napoli et al. Introduction of a chimeric chalcone synthase gene into petunia results in reversible co–suppression of homologous genes in trans. The Plant Cell. 2:279–289, Apr. 1990.*

Smith et al. Antisene RNA inhibition of polygalacturonase gene expression in transgenic tomatoes. Nature. 334:724–726, Aug. 1988.*

Wang et al. Identification and characterization of cDNAs encoding ethylene biosynthetic enzymes from Pelargonium x hortorum cv. Snow Mass Leaves. Plant Physiology. 109:627–636, Oct. 1995.*

Webster's II Dictionary, p. 1277, 1994.*

Seymour et al., "Down–regulation of two non–homologous endogenous tomato genes with a single chimeric sense gene construct", 1993, *Plant Molecular Biology*, 23:1–9.

de Borne et al., "Co–suppression of nitrate reductase host genes and transgenes in transgenic tobacco plants", 1994, *Mol. Gen. Genet.*, 243:613–621.

(List continued on next page.)

Primary Examiner—Lynette R. F. Smith
Assistant Examiner—Amy J. Nelson
(74) Attorney, Agent, or Firm—Akin, Gump, Strauss, Hauer & Feld, L.L.P.

(57) ABSTRACT

New ACC synthase genes from pineapple are disclosed which have utility as targets for the generation of transgenic plants in which the expression of ACC synthase is substantially controlled to effect the regulation of plant development, and, in particular, initiation of natural flowering.

36 Claims, 6 Drawing Sheets

OTHER PUBLICATIONS

Van Blokland et al., "Transgene–mediated suppression of chalcone synthase expression in *Petunia hybrida* results from an increase in RNA turnover", 1994, *The Plant Journal*, 6(6):861–877.

Angenent et al., "Co–suppression of the petunia homeotic gene fbp2 affects the identity of the generative meristem", 1994, *The Plant Journal*, 5(1):33–44.

Oeller et al., "Reversible Inhibition of Tomato Fruit Senescence by Antisense RNA", 1991, *Science*, 254:437–439.

Gaffe et al., "Pectin Methylesterase Isoforms in Tomato (*Lycopersicon esculentum*) Tissues", 1994, *Plant Physiol.*, 105:199–203.

Watson et al.,"Reduction of Tomato Polygalacturonase β Subunit Expression Affects Pectin Solubilization and Degradation during Fruit Ripening", 1994, *The Plant Cell*, 6:1623–1634.

Carrington et al., "Cell Wall Metabolism in Ripening Fruit", 1993, *Plant Physiol.* 103:429–434.

Kuipers et al.,"Formation and Deposition of Amylose in the Potato Tuber Starch Granule are Affected by the Reduction of Granule–Bound Starch Synthase Gene Expression", 1994, *The Plant Cell*, 6:43–52.

Bourque, June E., "Antisense strategies for genetic manipulations in plants", 1995, *Plant Science*, 105:125–149.

* cited by examiner

```
F   Q   D   Y   H   G   L   K   T   F   R   K   A   M   A   S   F   M   E   Q
TTCCAGGACTACCATGGGCTAAAAACTTTTAGAAAGGCAAGTTTTATGGAGCAA                          60

I   R   G   G   K   A   K   F   D   P   D   R   I   V   L   A   G   G   A   T
ATAAGAGGAGGAAAGGCTAAATTCGACCCGGATTGTTCTCGCGGGAGGCGCAACC                         120

A   A   N   G   L   L   T   F   I   L   A   D   P   G   D   A   L   L   I   P
GCCGCGAATGGGCTATTGACTTTCATATTAGCAGATCCTGGAGATGCTTTACTGATTCCG                    180

T   P   Y   Y   P   G   F   D   R   D   L   R   W   R   T   G   V   N   I   V
ACTCCGTATTATCCAGGATTCGATAGAGATTTGAGATGGAGAACCGGCGTGAACATCGTT                    240

P   I   R   C   D   S   S   N   G   F   Q   V   T   L   K   A   L   E   A   A
CCAATCCGATGCGACAGTTCAAACGGATTCCAAGTCACTCTCAAAGCCTTAGAAGCCGCT                    300

Y   A   K   A   E   A   A   E   M   K   V   R   G   V   L   L   T   N   P   S
TACGCCAAGGCAGAAGCGGCGGAGATGAAAGTCAGAGGGGTTCTCCTGACGAACCCGTCG                    360

N   P   L   G   T   A   V   D   R   A   V   L   E   D   I   L   D   F   A   A
AACCCGCTGGGCACCGGCGTCGACAGGGCGGTCCTGGAAGACATACTAGACTTCGCCGCC                    420

R   K   D   I   H   S   I   S   D   E   I   Y   S   G   S   V   F   A   S   P
CGGAAGGACATCCACTCGATATCCGACGAGATCTACTCGGGCTCGGTCTTCGCCTCTCCG                    480
```

```
                                                                        540
E  F  D  S  V  G  E  I  V  E  A  R  G  Y  R  I  C  E  R  V
GAGTTCGACAGCGTGGGGGAGATCGTCGAGGCGCGGGGCTACCGCATCTGCGAGAGGGTA

600
H  I  V  Y  S  L  S  K  D  L  G  L  P  G  F  R  V  G  T  I
CACATTGTCTACAGCCTCTCCAAGGACTTAGGCCTCCCCGGTTTTAGGGTTGGGACGATC

660
Y  S  Y  N  N  R  V  V  T  A  R  R  M  S  S  F  T  L  V
TATTCATACAACAATAGGGTGGTGACCGCGAGGAGGATGTCGAGCTTCACACTCGTG

720
S  S  Q  T  Q  K  T  L  A  S  M  L  S  D  E  E  F  T  K  Y
TCGTCGCAGACTCAGAAGACGCTGGCGTCGATGCTGTCGGACGAGGAGTTCACAAAGTAC

780
Y  I  R  T  N  R  E  R  L  K  R  R  Y  E  Y  I  Q  G  L
TACATAAGGACCAACAGGGAGAGGCTGAAGAGGAGGTACGAGTACATAATCCAGGGGCTG

840
E  R  A  G  I  E  C  F  Q  G  N  A  G  L  F  C  W  M  N  L
GAGAGAGCAGGGATTGAGTGCTTCCAAGGAAATGCCGGGCTGTTCTGCTGGATGAATCTG

900
G  P  L  L  E  E  Q  T  R  E  G  E  L  S  L  W  K  L  I  L
GGGCCACTCCTGGAGGAGCAGACGAGAGAAGGGGAGCTCAGCCTGTGGAAACTGATATTG
```

```
                H  E  V  R  L  N  I  S  P  G  S  S  C  H  C  S  E  P  G  W
             CATGAGGTGAGGCTCAACATATCACCAGGATCTTCATGCCACTGCTCTGAGCCTGGCTGG      960

F  R  V
             TTCCGTGT    968
```

FIG. 1C

```
                T  R  N  Q  P  G  S  T  S  A  N  E  I  L  I  F  C  L  G  E
             ACCCGAAACCAGCCTGGCTCTACTTCCGCAAATGAGATTCTCATTTTCTGCCTCGGCGAA       60

P  G  D  A  F  L  V  P  T  P  Y  Y  P  G
             CCTGGCGACGCGTTCCTCGTTCCAACTCCTTACTACCCTGGgtaagtactatacatattc      120 actcctatatattaatatgtctcttcttgtacgttttcccatgtatactaaatatgct       180

F  D  R  D  L  K  W  R  T  G  A  E  I  I  P
             gtttaacttgcagGTTTGATAGGGATCTCAAATGGCGACTGGTGCCGAGATCATACCGA      240

I  H  C  S  S  S  G  F  R  I  T  K  P  A  L  E  E  A  Y
             TCCACTGCTCGAGCTCGAGCGGGTTTCGGATCACCAAACCCGCGCTCGAAGAGGCTTATC      300
```

FIG. 2A

```
H  Q  A  Q  Q  Q  K  L  R  V  K  G  V  L  V  T  N  P  S  N
ATCAAGCTCAGCAGCAGAAGCTAAGAGTGAAGGAGTGTTGGTCACCAACCCCTCGAACC      360

P  L  G  T  T  L  V  H  R  E  L  E  T  L  I  D  F  I  V  A
CTTTGGGCACCACATTGGTGCACCGTGAGCTAGAAACCCTAGAAAACTCGACTTCATTGTGGCCA  420

K  G  I  H  L  I  S  D  E  I  Y  S  G  T  N  C  D  S  P  G
AAGGCATCCATCTGATCAGCGATGAGATATACTCCGGCACCAACTGCGACTCTCCGGGTT    480

F  I  S  V  A  E  A  I  T  E  R  G  E  E  V  A  D  R  V  H
TCATAAGTGTCGCTGAGGCGATAACCGAACGAGGCGAAGAGTGGCGGACCGTGTACACA     540

I  V  Y  S  L  S  K  D  L  G  L  P  G  F  R  V  G  A  I  H
TCGTGTATAGCTTATCGAAGGACCTCGGGCTACCAGGCTTTCGCGTCGGTGCGATACACT   600

S  Q  N  E  A  V  V  S  T  A  T  K  M  S  S  F  G  L  I  S
CCCAAAATGAGGCGGTGGTCTCCACGGCGACCAAGATGTCGAGCTTTGGGCTCATCTCT    660

S  Q  T  Q  Y  F  L  S  L  L  L  S  D  K  E  F  T  A  N  Y
CTCAAACTCAGTACTTCTTGTCCTTGTTGCTCTCCGACAAGGAGTTCACAGCGAACTACA   720

I  A  E  N  K  K  R  L  R  E  R  Q  K  R  L  T  E  A  L  R
TAGCGGAGAACAAGAAGCGGCTTAGAGAGCGGCAAAAGCGGCTCACCGAAGCGCTGCGGA   780
```

FIG. 2B

```
T  I  G  I  N  C  L  E  S  N  A  G  L  F  C  W  V  D  M  R
CGATCGGTATAAACTGTTTGGAGAGCAATGCAGGGTTGTTTTGTTGGTGGACATGAGGC    840

H  L  L  K  S  K  T  P  E  G  E  M  E  L  W  K  R  I  V  H
ACTTACTTAAGTCTAAGACACCTGAAGGAGAGATGGAGCTGTGGAAAAGGATAGTGCATG   900

D  V  G  L  N  I  S  P  G  S  S  T  Q  R  P  G  W  F  R
ATGTGGGACTAAACATTTCTCCGGGCTCTTCGTCCACTCAACGACCTGGCTGGTTCCGCG   960

ACC SYNTHASE GENES FROM PINEAPPLE

FIELD OF THE INVENTION

THIS INVENTION relates to ACC synthase and, in particular, novel ACC synthase genes derived from pineapple.

BACKGROUND OF THE INVENTION

Ethylene is one of five well-established plant hormones. It plays an important role in virtually every phase of plant development including seed germination, fruit ripening, leaf and flower senescence, and abscission. The production of ethylene may also be induced by external factors such as mechanical wounding, anaerobiosis, auxin treatment, ultraviolet light, temperature extremes, water stress, and ions such as cadmium, and lithium (Abeles, F. B., 1973, Ethylene in Plant Biology, 197–219, Academic Press, London; Yang & Hoffman, 1984, *Annu. Rev. Plant Physiol.*, 35, 155–189).

The pathway for ethylene biosynthesis has been established, the first step of which involves the formation of S-adenosyl-L-methionine (AdoMet) by S-adenosyl-L-methionine synthetase. AdoMet is subsequently converted by S-adenosyl-L-methionine methylthio-adenosine-lyase (ACC synthase; EC 4.4.1.14) to the nonprotein amino acid 1-aminocyclopropane-1 carboxylic acid (ACC), the immediate precursor of ethylene in higher plants (Adams & Yang, 1979, *Proc. Natl. Acad. Sci. USA*, 76, 170–174). Physiological analysis has suggested that this is the key regulatory step in the pathway, (Kende, 1989, Plant Physiol., 91, 1–4). Thus, the rate of endogenous expression of ACC synthase is considered to limit substantially the rate of ethylene production.

It is well known that endogenous ethylene is often deleterious to crops. In particular, increased ethylene production due to trauma caused by mechanical wounding of fruits and vegetables, and the cutting of flowers greatly diminishes their post harvest quality and storage life. However, the role of ethylene in regard to initiation of flowering in plants is not so clear. In this respect, ethylene is known to inhibit flowering in most plant species but in regard to mango and species of Bromeliad including pineapple, ethylene has been shown to promote initiation of flowering (Salisbury and Ross, 1992, *Plant Physiology*, Wadsworth Inc., California, p. 682). Accordingly, ethylene, ethylene producing compounds and auxins have been used almost universally to artificially induce flowering in commercial pineapple production (Turnbull et al, 1993, *Acta Horticulturae*, 334, 83–92).

However, flower initiation in pineapple can occur naturally once a minimum plant size and age is attained (Py et al, 1987, "The Cultivation of Pineapple", G. P. Maisonneuve Et Larose, Paris, p. 567; Bartholomew and Malezieux, 1994 In Schaffer and Anderson, 1994, "Handbook of Environmental Physiology of Fruit Crops, CRC Press, Florida, p. 310). This generally causes problems because if natural flower initiation occurs in a portion of the crop before the application of ethylene producing compounds thereto, crop control will only be partial.

In many countries, natural flowering of pineapple plants is a major industry problem because a substantial portion of a particular crop flowers naturally at different times in comparison to the remainder of the crop which has been induced artificially. For example, in Australia, natural initiation of flowering usually causes 5 to 40% of a summer crop to produce fruit which matures 4 to 6 weeks ahead of the normal summer harvest. This increases the number of passes required to pick that crop and generally results in some fruit being over-ripe. These factors decrease substantially the profits associated with growing a pineapple crop. Furthermore, cost benefits that would be possible if crop harvests could be planned completely cannot be achieved because a grower must artificially induce a crop at times designed to circumvent natural initiations.

Accordingly, the control of flowering to thereby control the timing and spread of fruit ripening within a crop is an important industry objective. If flowering and hence the uniformity of fruit maturity within the crop can be better controlled, fewer passes will be necessary to pick the fruit, and less fruit will be lost as a consequence of over-ripeness or immaturity. Furthermore, the control of flowering and hence fruit maturity will assist substantially in the organisation of labour associated with harvesting and processing activities and allow more flexibility in planning crop schedules (Py et al, 1987, supra).

At the present time, there are no satisfactory means for the prevention of natural flowering in pineapple plants. However, a strategy has been developed recently that takes advantage of the modulation properties of ACC synthase in the control of ethylene biosynthesis. In this regard, reference may be made to International Application No. PCT/US91/06453 which is directed to inhibition of expression of endogenous ACC synthase using an antisense expression system. This system comprises a DNA molecule capable of generating, when contained in a plant host cell, a complementary RNA that is sufficiently complementary to an RNA transcribed from an endogenous ACC synthase gene to prevent the synthesis of endogenous ACC synthase. Ethylene production in fruits of transgenic tomato plants engineered using this system was inhibited by 99.5% and, as a consequence, fruit ripening was suppressed. In addition, the application of ethylene or propylene to the fruits of these plants restored normal ripening.

Thus, ACC synthase genes may be used as targets for the generation of transgenic plants in which endogenous expression of ACC synthase is inhibited to effect suppression of ethylene production. The efficacy of this system, however, is predicated on the condition that the antisense RNA is sufficiently complementary to the transcript expressed from the target gene. In this regard, many studies have shown that ACC synthase is encoded by a highly divergent multigene family (for a review, see Theologis, A. 1992, *Cell*, 70, 181–184; Kende, H., 1993, *Annu. Rev. Plant Physiol. Plant Mol. Biol.*, 44, 283–307). Accordingly, if there is diversity between different ACC synthase genes, the use in this system for example, of a particular ACC synthase gene from one plant species would not be expected to inhibit the expression of an ACC synthase gene from another plant species. This is supported on page 5 of PCT/US91/06453 which states that "[w]hile the various ACC synthases are generally active in a variety of plant tissues, the DNAs are not completely homologous, and therefore the use of the genetic materials for control of synthesis, for example, using an antisense strategy, does not translate cross species."

In addition to sequence diversity of ACC synthases across species, it is well known that there is substantial sequence diversity of ACC synthases encoded within species. For example, in tomato, ACC synthase is encoded by six genes, two of which are expressed in fruit ripening (Van der Straeten et al., 1990, *Proc. Natl. Acad. Sci. USA*, 87, 4859–4863; Olson et al., 1991, *Proc. Natl. Acad. Sci. USA*, 88, 5340–5344; Rottmann et al., 1991, *J. Mol. Biol.*, 222, 937–961; Yipp et al., 1992, *Proc. Natl. Acad. Sci. USA*, 89, 2475–2479). The other four ACC synthases have been purported to be involved in other stages of plant development.

Reference also may be made to an article by Sato and Theologis (1989, *Proc. Natl. Acad. Sci. USA,* 86, 6621–6625) which describes the presence of a number of homologous but different ACC synthases in zucchini. In this regard, the various ACC synthases were shown to control ethylene production during different developmental processes, thus permitting separate control of, for example, fruit ripening and seed germination.

Accordingly, if there is diversity between different ACC synthase genes within plant species, the use, for example, of a particular ACC synthase gene involved in one stage of plant development in the antisense system of PCT/US91/06453 would not be expected necessarily to inhibit the expression of an ACC synthase gene involved in another stage of plant development.

OBJECT OF THE INVENTION

It is therefore an object of the present invention to provide new ACC synthase genes which have utility as targets for the generation of transgenic plants in which the expression of ACC synthase is substantially controlled to effect the regulation of plant development, and in particular, initiation of flowering.

It is a further object of the invention to provide a method for isolation of ACC synthase genes involved in the regulation of floral initiation of a plant.

SUMMARY OF THE INVENTION

In one aspect of the invention, there is provided an isolated nucleotide sequence, exemplified by SEQ ID NO:1, encoding a first ACC synthase enzyme of pineapple comprising the sequence of amino acids (SEQ ID NO:2) as shown in FIG. 1.

In another aspect of the invention, there is provided an isolated nucleotide sequence, exemplified by SEQ ID NO:3, encoding a second ACC synthase enzyme of pineapple comprising the sequence of amino acids (SEQ ID NO:4) as shown in FIG. 2.

The term "nucleotide sequence" as used herein designates mRNA, RNA, cRNA, cDNA or DNA. One of skill in the art will appreciate that cDNA is complementary DNA produced from a RNA template, usually by the action of RNA-dependent DNA polymerase (reverse transcriptase). If the RNA template has not been processed to remove the introns, the cDNA will be identical to the gene from which the RNA was transcribed.

The invention also provides homologs of the nucleotide sequences of the invention, exemplified by SEQ ID NO:1 and SEQ ID NO:3, respectively described in FIGS. 1–2. Such "homologs", as used in this specification include all nucleotide sequences encoding sub-sequences of the nucleotide sequences FIGS. 1–2.

The homologs of the invention further comprise nucleotide sequences that hybridize with any one of the nucleotide sequences of the invention under stringent conditions. Suitable hybridization conditions are discussed below.

The homologs of the invention may be prepared according to the following procedure:

(i) designing primers which are preferably degenerate which span at least a fragment of a nucleotide sequence of the invention; and (ii) using such primers to amplify, via nucleotide sequence amplification techniques, said at least a fragment from a nucleic acid extract obtained from a suitable host. Suitable nucleotide sequence amplification techniques are well known to those of skill in the art and include, for example, the Polymerase Chain Reaction (PCR), Strand Displacement Amplification (SDA) and Rolling Circle Replication (RCR). The suitable host from which a nucleic acid extract is obtained is preferably a cell or tissue obtained from a pineapple plant, preferably a D leaf of the pineapple plant, more preferably a basal white portion of the D leaf. By "obtained from" is meant that the nucleic acid extract is isolated from, or derived from, a particular source of the host. For example, the nucleic acid extract may be obtained from cells or tissue isolated directly from a pineapple plant. In such a case., the cells or tissue are preferably derived from a D leaf of the pineapple plant, more preferably the basal white portion of the D leaf. Alternatively, the cells or tissue may be derived from a stem apex of the pineapple plant.

Alternatively, a homolog of the invention may be obtained from a nucleotide sequence library derived from pineapple tissue. Such a library may be a pineapple cDNA library.

"Hybridization" is used here to denote the pairing of complementary nucleotide sequences to produce a DNA—DNA hybrid or a DNA-RNA hybrid. Complementary base sequences are those sequences that are related by the base-pairing rules. In DNA, A pairs with T and C pairs with G. In RNA, U pairs with A and C pairs with G.

Typically, nucleotide sequences to be compared by means of hybridization are analyzed using dot blotting, slot blotting, or Southern blotting. Southern blotting is used to determine the complementarity of DNA sequences. Northern blotting determines complementarity of DNA and RNA sequences or RNA and RNA sequences. Dot and Slot blotting can be used to analyze DNA/DNA, DNA/RNA or RNA/RNA complementarity. These techniques are well known by those of skill in the art. Typical procedures are described in CURRENT PROTOCOLS IN MOLECULAR BIOLOGY (Ausubel, et al., eds.) (John Wiley & Sons, Inc. 1995) at pages 2.9.1 through 2.9.20. Briefly, for Southern blotting, DNA samples are separated by size using gel electrophoresis. The size-separated DNA samples are transferred to and immobilized on a membrane (typically, nitrocellulose) and the DNA samples are probed with a radioactively or enzymatically or fluorochromatically labeled complementary nucleic acid. In dot blotting and slot blotting, DNA samples are directly spotted onto a membrane (nitrocellulose or nylon). The membrane is then probed with a labeled complementary nucleic acid.

Typically, the following general procedure can be used to determine hybridization under stringent conditions. A nucleotide according to the invention (such as the nucleotide sequence of FIGS. 1 (SEQ ID NO:1) or 2 (SEQ ID NO:13) or a sub-sequence thereof) will be immobilized on a membrane using one of the above-described procedures for blotting. A sample nucleotide sequence will be labeled and used as a "probe." Using procedures well known to those skilled in the art for blotting described above, the ability of the probe to hybridize with a nucleotide sequence according to the invention can be analyzed.

A probe is a biochemical labeled with a radioactive isotope or tagged in other ways for ease in identification. A probe is used to identify a gene, a gene product or a protein. Thus a nucleotide sequence probe can be used to identify complementary nucleotide sequences. An mRNA probe will hybridize with its corresponding DNA gene.

One of skill in the art will recognize that various factors can influence the amount and detectability of the probe bound to the immobilized DNA. The specific activity of the probe must be sufficiently high to permit detection. Typically, a specific activity of at least $10^8$ dpm/μg is necessary to avoid weak or undetectable hybridization signals when using a radioactive hybridization probe. A probe with a specific activity of $10^8$ to $10^9$ dpm/μg can detect approximately 0.5 pg of DNA. It is well known in the art that sufficient DNA must be immobilized on the membrane to permit detection. It is desirable to have excess immobilized DNA and spotting 10 μg of DNA is generally an acceptable amount that will permit optimum detection in most circumstances. Adding an inert polymer such as 10% (w/v) dextran sulfate (mol. wt. 500,000) or PEG 6000 to the hybridization solution can also increase the sensitivity of the hybridization. Adding these polymers has been known to increase the hybridization signal. See Ausubel, supra, at p 2.10.10.

To achieve meaningful results from hybridization between a first nucleotide sequence immobilized on a membrane and a second nucleotide sequence to be used as a hybridization probe, (1) sufficient probe must bind to the immobilized DNA to produce a detectable signal (sensitivity) and (2) following the washing procedure, the probe must be attached only to those immobilized sequences with the desired degree of complementarity to the probe sequence (specificity).

"Stringency," as used in this specification, means the condition with regard to temperature, ionic strength and the presence of certain organic solvents, under which nucleic acid hybridizations are carried out. The higher the stringency used, the higher will be the degree of complementarity between the probe and the immobilized DNA.

"Stringent conditions" designates those conditions under which only nucleotide sequences that have a high frequency of complementary base sequences will hybridize with each other.

Exemplary stringent conditions are (1) 0.75 M dibasic sodium phosphate/0.5 M monobasic sodium phosphate/1 mM disodium EDTA/1% sarkosyl at about 42° C. for at least about 30 minutes, (2) 6.0 M urea/0.4% sodium lauryl sulfate/0.1% SSC at about 42° C. for at least about 30 minutes, (3) 0.1× SSC/0.1% SDS at about 68° C. for at least about 20 minutes, (4) 1× SSC/0.1% SDS at about 55° C. for about one hour, (5) 1× SSC/0.1% SDS at about 62° C. for about one hour, (6) 1× SSC/0.1% SDS at about 68° C. for about one hour, (7) 0.2× SSC/0.1% SDS at about 55° C. for about one hour, (8) 0.2× SSC/0.1% SDS at about 62° C. for about one hour, and (9) 0.2× SSC/0.1% SDS at about 68° C. for about one hour. See, e.g. CURRENT PROTOCOLS IN MOLECULAR BIOLOGY (Ausubel, et al., eds.) (John Wiley & Sons, Inc. 1995), pages 2.10.1–2.10.16 of which are hereby incorporated by reference and Sambrook, et al., MOLECULAR CLONING. A LABORATORY MANUAL (Cold Spring Harbor Press, 1989) at §§1.101–1.104.

Stringent washes are typically carried out for a total of about 20 minutes to about 60 minutes. In certain instances, more than one stringent wash will be required to remove sequences that are not highly similar to nucleotide sequences according to FIGS. 1–2 (respectively, SEQ ID NO:1 and SEQ ID NO:3) or a sub-sequence thereof. Typically, two washes of equal duration, such as two 15 or 30 minute washes, are used. One of skill in the art will appreciate that other longer or shorter times may be employed for stringent washes to ensure identification of sequences similar to the nucleotide sequences of FIGS. 1–2 (respectively, SEQ ID NO:1 and SEQ ID NO:3) or sub-sequences thereof.

While stringent washes are typically carried out at temperatures from about 42° C. to about 68° C., one of skill in the art will appreciate that other temperatures may be suitable for stringent conditions. Maximum hybridization typically occurs at about 20 to about 25° C. below the $T_m$ for DNA—DNA hybrids. It is well known in the art that $T_m$ is the melting temperature, or temperature at which two nucleotide sequences dissociate. Methods for estimating $T_m$ are well known in the art. See, e.g. Ausubel, supra, at page 2.10.8. Maximum hybridization typically occurs at about 10 to about 15° C. below the $T_m$ for DNA-RNA hybrids.

Other typical stringent conditions are well-known in the art. One of skill in the art will recognize that various factors can be manipulated to optimize the specificity of the hybridization. Optimization of the stringency of the final washes can serve to ensure a high degree of hybridization between the nucleotide sequences according to FIGS. 1–2 (respectively, SEQ ID NO:1 and SEQ ID NO:3) or sub-sequences thereof and other similar nucleotide sequences.

In a typical hybridization procedure, DNA is first immobilized on a membrane such as a nitrocellulose membrane or a nylon membrane. Procedures for DNA immobilization on such membranes are well known in the art. See, e.g., Ausubel, supra at pages 2.9.1–2.9.20. The membrane is prehybridized at 42° C. for 30–60 minutes in 0.75 M dibasic sodium phosphate/0.5 M monobasic sodium phosphate/1 mM disodium EDTA/1% sarkosyl. Membranes are then hybridized at 42° C. in ACES hybridization solution (Life Technologies, Inc., Gaithersburg, Md.) containing labeled probe for one hour. Next, membranes are subjected to two high stringency 10 minute washes at 42° C. in 0.75 M dibasic sodium phosphate/0.5 M monobasic sodium phosphate/1 mM disodium EDTA/1% sarkosyl. Following this, the membranes are washed with 2× SSC at room temperature, to remove unbound probe.

In another typical hybridization procedure, DNA immobilized on a membrane is hybridized overnight at 42° C. in prehybridization solution. Following hybridization, blots are washed with two stringent washes, such as 6.0 M urea/0.4% sodium lauryl sulfate/0.1% SSC at 42° C. Following this, the membranes are washed with 2× SSC at room temperature.

Autoradiographic techniques for detecting radioactively labeled probes bound to membranes are well known in the art.

The invention further includes within its scope synonymous nucleotide sequences that encode for the ACC synthase enzymes or portions thereof shown in FIG. 1 (SEQ ID NO:3) and FIG. 2 (SEQ ID NO:4).

In yet another aspect of the invention, there is provided a method for obtaining a DNA sequence encoding at least a portion of an ACC synthase enzyme involved in the regulation of floral initiation of a plant, said method including the steps of:
  (a) inducing the production of the ACC synthase enzyme in cells or tissue of the plant;
  (b) preparing RNA from said cells or tissue resulting from step (a);
  (c) reverse transcribing the RNA to produce a cDNA transcript; and
  (d) isolating the DNA sequence from the cDNA transcript.

In regard to step (a), the production of the ACC synthase enzyme may be induced by any suitable technique. For example, the cells or tissue of the plant may be subjected to mechanical wounding, anaerobiosis, auxin treatment, ultraviolet light, temperature extremes such as for example cold shock, water stress, or ions such as cadmium, and lithium. Alternatively, the cells or tissue may be treated with ethylene, propylene, acetylene or ETHEPHON. Preferably, the cells or tissue are treated with auxins such as, for example, indoleacetic acid (IAA) or sodium α-naphthalene acetate.

Suitably, the plant is a species wherein one or more of the techniques described in regard to step (a) promotes initiation of flowering in the species. Preferably, the species is selected from mango species and species of Bromeliad such as, for example, pineapple.

The cells or tissue, from which RNA is prepared, may be derived from any suitable cells or tissue which produce an ACC synthase enzyme involved in the regulation of flowering.

In the case of pineapple, the cells or tissue are preferably derived from a D leaf of a pineapple plant, more preferably a basal white portion of the D leaf. Alternatively, the cells or tissue may be derived from a stem apex of the pineapple plant.

Preferably, the production of the ACC synthase enzyme in the cells or tissue of the plant is confirmed by suitable assay of ACC synthase activity such as for example described in an article by Lizada and Yang (1979, *Anal. Biochem.*, 100,140–145).

The term "RNA" as used herein refers to total RNA or poly-A$^+$ RNA.

Total RNA may be extracted in any suitable manner. For example, the plant or tissue resulting from step (a) may be homogenised and subsequently lysed in an appropriate lysis buffer. A suitable RNA preserving compound such as guanidinium isothiocyanate may also be added to the homogenate to prevent RNase-mediated digestion of the RNA. Total RNA may subsequently be isolated from the resulting homogenate by any suitable technique such as by ultracentrifugation through a $CsCl_2$ cushion or as described in Sambrook et al. (1989, "Molecular Cloning: A Laboratory Manual", 2nd Edition, Cold Spring Harbour, New York, Cold Spring Harbour Laboratory Press) which is hereby incorporated by reference. Alternatively, total RNA may be isolated using other suitable methods such as for example those described in articles by Logemann et al. (1987, *Anal. Biochem.*, 163, 16–20), Lopez-Gomez and Gomez-Lim (1992, *Hortscience*, 27, 440–442), Schultz et al. (1994, *Plant Mol. Biol. Reporter*, 12, 310–316), and Su and Gibor, 1988 (*Anal. Biochem.*, 174, 650–657) which articles are hereby incorporated by reference. Preferably, the total RNA is isolated according to a method described in Example 2.

Once total RNA has been extracted, by whichever method, poly-A$^+$ RNA may then be isolated from the total RNA, for example, by affinity chromatography on a compound containing multiple thymidine or uracil residues, to which the poly-A$^+$ tail of an messenger RNA (mRNA) can bind. Examples of suitable compounds include oligo-dT cellulose and poly-U SEPHADEX™. Poly-A$^+$ RNA can then be eluted by a suitable buffer.

Reverse transcription of the RNA resulting from step (b) may be effected using a standard technique based on conversion of RNA to first strand cDNA in the presence of a reverse transcriptase enzyme, an oligonucleotide primer complementary to the RNA and a mixture of deoxyribonucleotide triphosphates (dNTPs) such as for example dATP, dGTP, dCTP and dTTP. The cDNA transcript may comprise first strand cDNA or double stranded cDNA. In the latter case, second strand cDNA complementary to said first strand cDNA may be produced by any suitable technique. Such techniques are well known to those of skill in the art.

The oligonucleotide primer used for reverse transcription may be an oligo-dT primer or an antisense primer common to multiple members of the ACC synthase family of genes. Preferably, the oligonucleotide primer is a degenerate antisense primer complementary to one or more genes of the ACC synthase gene family.

In regard to step (d), the DNA sequence may be isolated using a suitable probe such as, for example, a nucleotide sequence encoding an ACC synthase enzyme of a plant, preferably from a species of Bromeliad such as pineapple. In such a case, hybridisation techniques as for example described above may be employed in concert with the probe to isolate the DNA sequence. Alternatively, the DNA sequence may be isolated using a nucleotide sequence amplification technique as for example referred to above. Preferably, the nucleotide sequence amplification technique is the Polymerase Chain Reaction (PCR). PCR may be carried out such as for example according to Sambrook et al. (1989, supra; in particular, Sections 14.14–14.20) which is hereby incorporated by reference. A standard PCR mix suitably comprises a thermostable DNA polymerase, two or more oligonucleotide primers, deoxyribonucleotide triphosphates, a suitable buffer and a DNA template to be amplified.

The thermostable DNA polymerase may comprise Taq DNA polymerase which may be the native enzyme purified from *Thermus aquaticus* and/or a genetically engineered form of the enzyme synthesised in *E. coli* sold under the trade mark AMPLITAQ™. Other commercially available polymerase enzymes include Taq polymerases marketed by Promega or Pharmacia. Another thermostable DNA polymerase that could be used is Tth DNA polymerase obtainable from *Thermus thermophilus*. Concentration ranges of the polymerase may range from 0.5–5.0 units per 100 μL of reaction mixture.

Deoxyribonucleotide triphosphates comprising dATP, dCTP, dGTP and dTTP (i.e. dNTPs) can be utilised in the assay with it being realised that dGTP may be substituted with 7-deaza-2'-deoxy GTP and 7-deaza-2'-deoxy ATP can be substituted for dATP. It will also be appreciated that 2'-deoxy ITP can be substituted for any dNTP. The four dNTPs may be present in a PCR reaction mixture at a concentration of 20–200 μM and at a pH of about 7.0.

Any suitable biological buffer may also be utilised in the reaction mixture such as Tris-HCl, or Tricine which can provide a pH in the range of 7.4–8.8. Tris-HCl may provide a pH of 8.3–8.8 at 20° C. and Tricine may provide a pH of 8.4. The concentration of buffer may be 10–50 mM in the case of Tris-HCl and around 300 mM in the case of Tricine.

The buffer may also comprise a source of $Mg^{2+}$ such as $MgCl_2$ which may affect (i) primer annealing (ii) strand dissociation temperatures of both template and PCR product, (iii) product specificity, (iv) formation of primer-dimer artifacts and (v) enzyme activity and fidelity. Taq polymerase may require free $Mg^{2+}$ on top of that bound by template DNA, primers and dNTPs. Accordingly the PCR mixture may contain 0.5–2.5 mM $Mg^{2+}$ over the total dNTP concentration.

The buffer may also include KCl in a concentration of up to 50 mM to facilitate primer annealing.

Another optional component may be β-mercaptoethanol in a concentration of 50 mM.

Gelatin or bovine serum albumin (BSA) may also be present in a concentration range of 0.01–0.1%.

Nonionic detergents such as Tween 20, Triton X-100, or Laureth 12 in a concentration range of 0.05 to 0.1% may also be added to help stabilise the enzyme.

The primer components may be present in the PCR reaction mixture at a concentration of between 0.1 and 1.0 μM. The primer length may be between 16–40 nucleotides in length and having 45–60% G and C composition.

In the choice of primer, it is preferable to have exactly matching bases at the 3' end of the primer but this requirement decreases to being relatively insignificant at the 5' end (this is described in *Nucleic Acids Research* 19, 3058). The preferred primers utilized in this invention are degenerate primers complementary to one or more genes of the ACC synthase gene family. More preferably, the primers are selected from the group, wherein "K" is G or T; "N" is A, C, G or T; "R" is A or G; and "Y" is C or T:
5'-TAYTTYGAYGGNTGGAARGC-3'(SEQ ID NO: 5);
5'-TCRTCCATRTTNGCRAARCA-3'(SEQ ID NO:6);
5'-CARATGGGNYTNGCNGARAA-3'(SEQ ID NO:7);
5'-GCRAARCANACNCYRAACCA-3'(SEQ ID NO:8);
5'-ACNCKRAACCANCCNGGYTC-3'(SEQ ID NO:9);
5'-TTYCARGAYTAYCAYGG-3'(SEQ ID NO:10).

It will be appreciated by those skilled in the art that nested PCR may also be used to improve the sensitivity and specificity of DNA amplification wherein the DNA fragment or fragments produced subsequent to a first round of PCR with a first primer pair are used as templates for a second round of PCR using nested primers internal to the first primer pair.

In the reaction conditions applicable to PCR, an initial denaturation step may be carried out between 90–100° C., a subsequent annealing step carried out between 40–60° C. and a final extension step may be carried out between 70–75° C. Alternatively the annealing step and extension step may be combined if considered appropriate.

The nucleotide sequences of the invention have utility as targets for the generation of transgenic variants of pineapple in which the expression of ACC synthase is substantially inhibited to effect suppression of flowering.

Accordingly, in a still further aspect of the invention, there is provided a method for generating a transgenic variety of pineapple in which natural initiation of flowering is substantially inhibited, said method including the steps of introducing into a pineapple plant, or plant part or cell thereof a vector comprising the nucleotide sequence of FIGS. 1 or 2 (respectively, SEQ ID NO:1 and SEQ ID NO:3) or homolog thereof wherein said nucleotide sequence is operably linked, in the sense orientation, to one or more regulatory nucleotide sequences, and growing said plant or plant part or cell thereof to generate the transgenic variety of pineapple.

The invention also comprises a method of generating a transgenic variety of pineapple in which natural initiation of flowering is substantially inhibited, said method including the steps of introducing into a pineapple plant, or plant part or cell thereof a vector comprising the nucleotide sequence of FIGS. 1 or 2 (respectively, SEQ ID NO:1 and SEQ ID NO:3) or homolog thereof wherein said nucleotide sequence is operably linked, in the antisense orientation, to one or more regulatory nucleotide sequences, and growing said plant or plant part or cell thereof to generate the transgenic variety of pineapple.

A vector according to the invention may be a prokaryotic or a eukaryotic expression vector, which are well known to those of skill in the art. Such vectors may contain one or more copies of the nucleotide sequences according to the invention.

Regulatory nucleotide sequences which may be utilized to regulate expression of the nucleotide sequences of FIGS. 1 or 2 (respectively, SEQ ID NO:1 and SEQ ID NO:3) or homolog thereof, but are not limited to, a promoter, an enhancer, and a transcriptional terminator. Such regulatory sequences are well known to those of skill in the art.

Suitable promoters which may be utilized to induce expression of the nucleotide sequences of the invention include constitutive promoters and inducible promoters. A particularly preferred promoter which may be used to induce such expression is the Cauliflower Mosaic Virus (CaMV) 35S promoter.

Any suitable transcriptional terminator may be used which effects termination of transcription of a nucleotide sequence in accordance with the invention. Preferably, the nopaline synthase (NOS) terminator, as for example disclosed in United States Patent Specification No. U.S. Pat. No. 5,034,322, is used as the transcription terminator.

The vector may also include a selection marker such as an antibiotic resistance gene which can be used for selection of suitable transformants. Examples of such resistance genes include the nptII gene which confers resistance to the antibiotics kanamycin and G418 (Geneticin®)) and the hph gene which confers resistance to the antibiotic hygromycin B.

The vector may be introduced by a number of methods including transfection, projectile bombardment, electroporation or infection by *Agrobacterium tumefaciens*.

With reference to the above methods wherein the nucleotide sequence is expressed in the sense orientation, such methods are predicated on RNA-mediated suppression (also termed gene-silencing or co-suppression) wherein transcription products of the nucleotide sequence which are substantially homologous to corresponding transcripts of an endogenous gene cause inhibition of expression of the endogenous gene. In this regard, reference may be made to WO 90/12084 (which is hereby incorporated by reference) which discloses methods for engineering transgenic plants based on RNA-mediated suppression.

With reference to the above methods wherein the nucleotide sequence is expressed in the antisense orientation, such methods are based on antisense-mediated'suppression as, for example, described in WO 92/04456 (which is hereby incorporated by reference).

It will of course be appreciated that gene transplacement by homologous recombination may also be used to effect the generation of suitable transgenic plants. Such methods are well known to persons of skill in the art.

In a still further aspect, the invention contemplates a transgenic variety of pineapple in which natural initiation of flowering is substantially inhibited, said variety comprising the nucleotide sequence of FIGS. 1 or 2 (respectively, SEQ ID NO:1 and SEQ ID NO:3) or homolog thereof wherein said nucleotide sequence is operably linked, in the sense orientation, to one or more regulatory nucleotide sequences.

In yet a still further aspect of the invention, there is provided a transgenic variety of pineapple in which natural initiation of flowering is substantially inhibited, said variety comprising the nucleotide sequence of FIGS. 1 or 2 (respectively, SEQ ID NO:1 and SEQ ID NO:3) or homolog thereof wherein said nucleotide sequence is operably linked, in the antisense orientation, to one or more regulatory nucleotide sequences.

The invention further contemplates pineapple fruit produced from such transgenic plants.

BRIEF DESCRIPTION OF THE DRAWINGS

FIGS. 1A–1C depict the nucleotide sequence (SEQ ID NO:1) and deduced amino acid sequence (SEQ ID NO:2) of acacc2.

FIGS. 2A–2D depict the nucleotide sequence (SEQ ID NO:3) and deduced amino acid sequence (SEQ ID NO:4) of acacc3.

DETAILED DESCRIPTION OF THE INVENTION

EXAMPLE 1

Figure 2D:
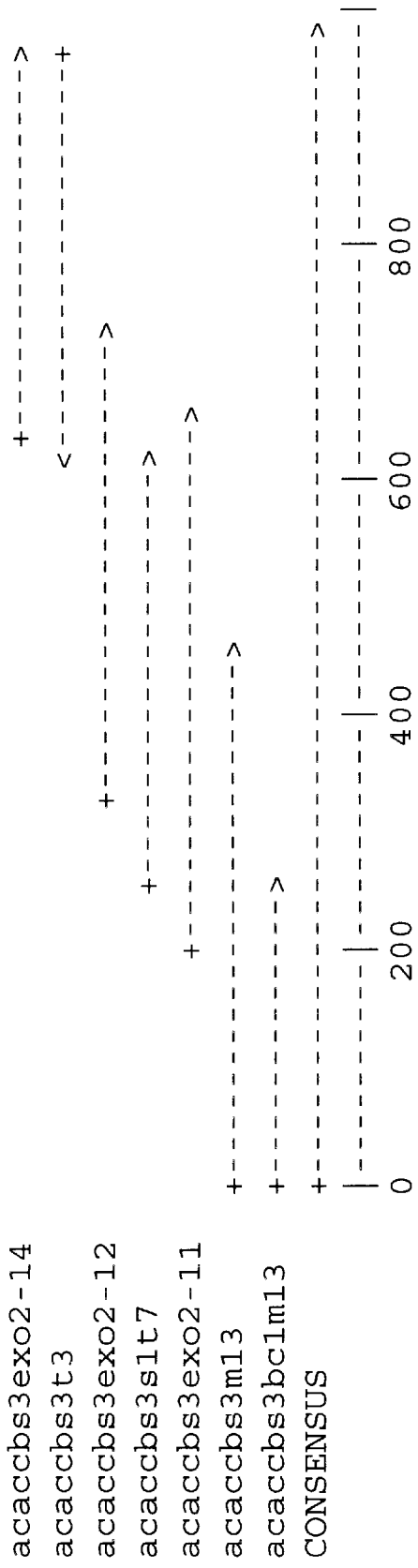

Treatment of Pineapple Plants with Sodium α-naphthalene acetate

Twelve month old field grown Smooth Cayenne pineapple plants [*Ananas comosus* (L.) Merr.], Clone 10, were treated with 0.2 mL/L of 245 g/L sodium α-naphthalene acetate solution in early April (autumn, southern hemisphere). Fifty-five to sixty milliliters of solution was applied to the heart of each plant.

Samples consisting of the basal white portion of the D leaf of 5 plants were collected on the day of treatment but prior to actual treatment of the plants and every day for 10 days thereafter.

The samples were wrapped in aluminium foil, marked with an identifying number and placed in liquid nitrogen within 1 minute of removal from the plant. These samples were stored subsequently at −70° C. until required. Subsequent observation of the treated plants in late August confirmed successful flower induction of all treated plants.

The samples were analysed for ACC content using the method of Lizada and Yang (1979, supra). One longitudinal half of each sample was used for assay of ACC content and the other half was retained for RNA extraction. Since ACC synthase has a short half-life, it would be reasonable to assume that samples having a high ACC content would also have a high level of ACC synthase activity. Thus, only samples having relatively high ACC content were used for RNA extraction and subsequent amplification of DNA sequences of the ACC synthase type by PCR.

EXAMPLE 2

Amplification of ACC Synthase Genes From Induced Tissue

Materials and Methods:

All glassware, utensils and centrifuge tubes were rinsed with water containing 0.1% diethyl pyrocarbonate (DEPC) and autoclaved in order to remove RNA degrading enzymes and protein contamination. Solutions were incubated with DEPC (0.1% final concentration) overnight and autoclaved to denature any RNases present in said solutions.

Nucleic Acid Extraction Procedure

In a liquid-nitrogen-filled mortar, tissue comprising basal white portion of the D leaf (1–4 g) was ground to a fine powder. While still frozen the powder was transferred to a 100 mL beaker containing 30 mL of lysis buffer (150 mM Tris pH 7.5 with boric acid, 2% SDS, 50 mM EDTA, 1% mercaptoethanol) and stirred for 5 min at room temperature. 0.25 volume of absolute ethanol and 0.11 volume of 5 M potassium acetate were added to the homogenate and stirred for a further 3 min. One volume of chloroform isoamyl alcohol (24:1) (SEVAG) was added subsequently and mixed for an additional 3 min. The homogenate was centrifuged at 18,000 rpm for 10 min in a prechilled (4° C.) centrifuge. The recovered aqueous phase was extracted twice with phenol-chloroform (1:1) or until no interphase (proteins and carbohydrates) was apparent.

After careful removal of the aqueous phase, nucleic acids were precipitated by the addition of 2.25 volumes of absolute ethanol. After incubation for 2 hrs at −20° C., nucleic acids were centrifuged for 30 min at 18,000 rpm, dried and redissolved in 10 mL of DEPC treated dH$_2$O. 8 M LiCl was added to a final concentration of 3 M and the mixture incubated overnight at −20 ° C. RNA was collected by centrifugation (18,000 rpm, for 30 min at 4° C.) and washed twice in 80% ethanol at room temperature and dried. The RNA pellet was resuspended subsequently in 300 μL of DEPC treated water, and RNA precipitated by adding sodium acetate to a final concentration of 0.3 M and 2.5 volumes of absolute ethanol. After overnight incubation at −70° C., the RNA was pelleted by centrifugation for 30 min at 14,000 rpm (4° C.). The pellet was washed twice in 80% ethanol and vacuum dried for 10 min. The RNA was then resuspended in 50 μL of DEPC treated sterile water, quantified spectrophotometrically and stored at −70° C.

Genomic DNA was pelleted from the supernatant collected after the LiCl precipitation step by the addition of 2 volumes of absolute ethanol, kept at −20° C. for 2 hrs and centrifuged at 12,000 rpm for 30 min. The DNA pellet was resuspended in 500 μL of TE buffer, quantified spectrophotometrically and stored at −20° C.

Formaldehyde Denaturing Gel Electrophoresis of RNA

Ten μg of total RNA was electrophoresed on a 1% agarose gel at 80 V for 1 hr. The gel was prepared by adding 0.5 g of agarose, 5 mL of 10× MOPS, 36 mL of DEPC treated water and 9 mL of formaldehyde. RNA samples were prepared by adding 25 μL of RNA loading buffer (containing ethidium bromide) to 5 μL of RNA and denatured at 70° C. for 5 min, followed by chilling on ice for 2 min. Electrophoresis was conducted in 1× MOPS buffer. The gel was photographed immediately after electrophoresis.

DNA Gel Electrophoresis

The integrity of genomic DNA was checked by electrophoresis on a 0.8% agarose gel (prepared in 1× TBE buffer) at 80 volts for 1 hr. 10× loading buffer was added to approximately 4 μg of DNA and electrophoresis conducted in 1× TBE buffer. The gel was stained in an ethidium bromide solution (66 μg/mL) and photographed as described above.

Design of Primers for Amplification of ACC Synthases From Higher Plants

Homology studies of several ACC synthase proteins revealed various conserved regions among this family of proteins. Those regions were used in designing degenerate oligonucleotides by reverse translating the amino acid sequence and taking in account the degeneracy of the genetic code. As a result, several degenerate oligonucleotides were synthesized and are shown in Table 1.

Amplification of acacc2

Reverse transcription of RNA was performed using 1 μg total RNA and 2.5 U of Moloney Murine Leukemia Virus (MMLV) reverse transcriptase in a reaction mixture of 10 mM Tris-HCl, pH 8.3 containing 50 mM KCl, 5 mM MgCl$_2$, 1 mM of each dNTP, 1 U RNase inhibitor and 2.5 μM of oligo-dT primer. The reaction mixture was incubated for 30 min at 42° C. and then heated to 99° C. for 5 min to inactivate the reverse transcriptase. The DNA resulting from this procedure was amplified using 2.5 U AMPLITAQ DNA Polymerase in a reaction mixture of 10 mM Tris-HCl, pH 8.3 containing 2 mM MgCl$_2$, 50 mM KCl, and 0.15 μM of EZ-5 (SEQ ID NO:7) and EZ-7 (SEQ ID NO:9) (Table 1). After an initial 3 min period of denaturation at 94° C., the PCR parameters were 1 min template denaturation at 94° C., 1 min primer annealing at 48° C. and 2 min primer extension at 72° C. for 45 cycles. A final extension step of 15 min at 72° C. was used subsequently to ensure full length amplification products.

The products of this PCR reaction were further amplified using a second set of oligonucleotide primers EZ-7 (SEQ ID NO:9) and EZ-8 (SEQ ID NO:10) (Table 1). The reaction consisted of adding to a tube a sample of the products obtained from the previous amplification and 2.5 U AMPLITAQ DNA Polymerase in a reaction mixture of 10 mM Tris-HCl, pH 8.3 containing 1.5 mM MgCl$_2$, 50 mM KCl, 0.2 mM of each dNTP, 0.1% gelatin and 0.15 μM of each primer in a total volume of 100 μL. The PCR parameters were 30 sec template denaturation at 94° C., 30 sec primer annealing at 48° C. and 1.5 min primer extension at 72° C. for 30 cycles. The PCR products were analysed on 0.8% agarose gels and visualized with ethidium bromide.

Subcloning and Sequencing of PCR Products

The DNA amplified by PCR was ligated into pBluescript (SK+) (Stratagene, La Jolla, Calif.). The ligation mixtures were used to transform E. coli DH5α. Transformants were selected on LB plates containing ampicillin (50 mg/mL) and X-gal (0.033% w/v). Plasmid DNA was isolated using the alkaline lysis method.

DNA sequencing was carried out using Applied Biosystems PRISM™ Ready Reaction DyeDeoxy™ Terminator Cycle Sequencing kit.

Results:

Agarose gel electrophoresis of the amplification products revealed the presence of a DNA band having a mobility corresponding with that of a 0.95 Kb DNA fragment. The DNA fragments corresponding to this band were subcloned into pBluescript and analysis of several recombinant plasmids revealed the presence of two different inserts of approximately the same length but with different restriction patterns. The two different clones were named acacc2 and acacc3 respectively.

The nucleotide sequence (SEQ ID NO:1) of acacc2 and the deduced amino acid sequence (SEQ ID NO:2) thereof are shown in FIG. 1. Comparison of these sequences with other published ACC synthase sequences indicates that acacc2 is a cDNA coding for a member of the ACC synthase family in pineapple. Searches in all the available protein and DNA data banks failed to find 100% homology with any existing clone. The highest homology found at the DNA level using the BLASTN program was 69% respectively with a *Vigna radiata* gene # Z12135 (EMBL data bank) and a *S. tuberosum* gene # Z27235 (EMBL data bank). Similarly, at the protein level, the highest homology found using the program BLASTX was 78% with a *Vigna radiata* ACC synthase, entry # PN0477 (PIR database).

The nucleotide sequence (SEQ ID NO:3) of acacc3 and the deduced amino acid sequence thereof are shown in FIG. 2. Nucleotide sequence analysis of acacc3 suggests that this DNA product was amplified either from small residual amounts of genomic DNA present in the RNA preparation or from heterologous nuclear RNA which had not been processed into mRNA.

Comparison of the nucleotide and deduced amino acid sequences of acacc3 with other published ACC synthase sequences indicates that acacc3 encodes a member of the ACC synthase family in pineapple. The highest homology found at the DNA level was 67% respectively with a *Malus sylvestris* mRNA clone # U083294 (GenBank database) and a *Malus domestica* mRNA clone # L31347 (GenBank database). At the protein level, the highest homology found was 75% with an ACC synthase from a Musa species, # e233391 (GenBank database).

Analysis of the above DNA sequences reveals that sizes of acacc2 and acacc3 are 968 bp and 961 bp respectively. Each of these DNA sequences represents approximately 75% of the coding region relating thereto.

EXAMPLE 3

Stable Integration and Expression of ACC Synthase Antisense Genes in Pineapple (*Ananas comosus* (L.) Merrill.)

Materials and Methods

Initiation of somatic embryogenesis

Meristems are excised from the crown of a pineapple fruit and placed on MS media (Murashige and Skoog, 1962, *Physiologia Plantarum*, 15:473–497) containing 2.5 mg/L 6-benzylamino purine (BAP). When subcultured at a two-weekly interval, buds/shoots start to proliferate after 3 to 5 months. Leaf base tissue or stem tissue is then excised and placed on callus media (Wakasa, K., 1989, In "Biotechnology in Agriculture and Forestry 5—Trees 11", Ed Bajaj, Y. P. S. Springer-Verlag, London) containing MS, 10 mg/L BAP and 10 mg/L sodium α-naphthalene acetate (NAA). In the case of leaf base material, callus forms in 24 to 34 days on over 60% of explants. In the case of stem tissue, callus will form on over 90% of explants in 13 to 24 days. Leaf explants are preferred as they produce callus of a higher quality with a greater proliferation rate.

Transformation vector

A transformation vector which may be utilised for generating a transgenic variety of pineapple, wherein expression of an ACC synthase enzyme is substantially inhibited, may be constructed by operably linking the nucleotide sequence of FIG. 1 (SEQ ID NO:1) or FIG. 2 (SEQ ID NO:3), in the antisense orientation, to a suitable promoter. The vector may also contain a selectable marker such as the kanamycin or hygromycin resistance gene. Plasmid DNA for microprojectile bombardment can be purified using the commercially available QIAGEN kit.

Bombardment conditions

Calli (embryos) are bombarded using a particle inflow gun (Finer, Vain, Jones, and McMullen, 1992, *Plant Cell Reports*, 11:323–328). Gold particles of 1–1.6 μm diameter (BioRad Laboratories, Hercules, Calif., USA) are used as microprojectiles wherein a quantity of particles is washed with 100% ethanol and three times with sterile water before resuspension in sterile water. For coating of microprojectiles, 50 μL of the gold suspension is mixed with 1.0 μg/μL plasmid DNA, 50 μL 2.5 M $CaCl_2$ and 20 μL 0.5 M spermidine free base. All solutions are kept at room temperature.

The suspension is vortexed for 5 minutes then allowed to settle for 1 minute then centrifuged for 10 secs at 13,000 G before 100 μL of the supernatant is removed and discarded. The remaining suspension is vortexed immediately before utilising 5 μL of the mixture for each bombardment.

Calli (embryos) are arranged, without overlap, in an area of approximately 20 mm diameter in the centre of a petri-dish. A protective baffle of stainless steel mesh with an aperture of 210 μm (Franks and Birch, 1991, *Aust. J. Plant Physiol.* 18, 471–480) is placed over the tissue during bombardment. The pressure of the helium blast is 800 to 1000 kPa and the distance to the target embryos from the filter unit containing the gold coated particles is 15 to 20 cm.

Selection and regeneration of transformed plantlets

Following bombardment, calli (embryos) are allowed to recover over several days on callus media, prior to selection on callus media containing kanamycin monosulfate (200 μg/mL) or hygromycin (20 μg/mL). Calli (embryos) are then selected for kanamycin or hygromycin resistance after several weeks on such media.

For germination, calli (embryos) are subsequently transferred to a shoot regeneration media (Mathews and Rangan, 1981, *Scientia Horticulturae* 14 227–234) containing MS, 5% coconut water and 400 mg/L casein hydrolysate. Within 1 to 2 months the callus will initiate shoots. Single plantlets are then transferred onto a rooting media (Wakasa, K., 1989, In "Biotechnology in Agriculture and Forestry 5 Trees II", Ed Bajaj, Y. P. S. Springer-Verlag, London.) containing MS and 1 mg/L NAA. Rooting will occur within 2 weeks and the plantlets are then transferred to MS media without hormones for further growth.

Initiation of flowering in such plants may be induced artificially, for example, by exogenous application of ETHEPHON, ethylene or propylene thereto.

The use of such methods, in concert with the nucleotide sequences, homologs or sub-sequences of the invention, enable the generation of transgenic pineapple varieties in which natural flowering is inhibited substantially. It is anticipated that such transgenic varieties will provide for substantial advantage because they could be induced to flower in a narrow spectrum of time which would thereby decrease the spread of fruit maturity within a crop. Accordingly, fewer passes would be necessary to pick the fruit, and less fruit would be lost as a consequence of over-ripeness or immaturity. Furthermore, the control of flowering in such transgenic pineapple varieties will assist substantially in the organisation of labour associated with harvesting and processing activities thereof and would be of great value where pineapple is harvested mechanically.

TABLE 1

Degenerate oligonucleotides designed to amplify ACC synthase genes and cDNAs from higher plants.

| | |
|---|---|
| EZ-2 | 5' TAYTTYGAYGGNTGGAARGC 3' (SEQ ID NO: 5) |
| EZ-4 | 5' TCRTCCATRTTNGCRAARCA 3' (SEQ ID NO: 6) |
| EZ-5 | 5' CARATGGGNYTNGCNGARAA 3' (SEQ ID NO: 7) |
| EZ-6 | 5' GCRAARCANACNCTRAACCA 3' (SEQ ID NO: 8) |
| EZ-7 | 5' ACNCKRAACCANCCNGGYTC 3' (SEQ ID NO: 9) |
| EZ-8 | 5' TTYCARGAYTAYCAYGG 3' (SEQ ID NO: 10) |

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 968 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS
      (B) LOCATION: 1..968

(xi) SEQUENCE DESCRIPTION: SEQ ID NO:1:

```
TTC CAG GAC TAC CAT GGG CTA AAA ACT TTT AGA AAG GCA ATG GCA AGT        48
Phe Gln Asp Tyr His Gly Leu Lys Thr Phe Arg Lys Ala Met Ala Ser
 1               5                  10                  15

TTT ATG GAG CAA ATA AGA GGA GGA AAG GCT AAA TTC GAC CCG GAC CGG        96
Phe Met Glu Gln Ile Arg Gly Gly Lys Ala Lys Phe Asp Pro Asp Arg
                20                  25                  30

ATT GTT CTC GCG GGA GGC GCA ACC GCC GCG AAT GGG CTA TTG ACT TTC       144
Ile Val Leu Ala Gly Gly Ala Thr Ala Ala Asn Gly Leu Leu Thr Phe
             35                  40                  45

ATA TTA GCA GAT CCT GGA GAT GCT TTA CTG ATT CCG ACT CCG TAT TAT       192
Ile Leu Ala Asp Pro Gly Asp Ala Leu Leu Ile Pro Thr Pro Tyr Tyr
         50                  55                  60

CCA GGA TTC GAT AGA GAT TTG AGA TGG AGA ACC GGC GTG AAC ATC GTT       240
Pro Gly Phe Asp Arg Asp Leu Arg Trp Arg Thr Gly Val Asn Ile Val
 65                  70                  75                  80

CCA ATC CGA TGC GAC AGT TCA AAC GGA TTC CAA GTC ACT CTC AAA GCC       288
Pro Ile Arg Cys Asp Ser Ser Asn Gly Phe Gln Val Thr Leu Lys Ala
                 85                  90                  95

TTA GAA GCC GCT TAC GCC AAG GCA GAA GCG GCG GAG ATG AAA GTC AGA       336
Leu Glu Ala Ala Tyr Ala Lys Ala Glu Ala Ala Glu Met Lys Val Arg
                100                 105                 110
```

```
GGG GTT CTC CTG ACG AAC CCG TCG AAC CCG CTG GGC ACC GCG GTC GAC      384
Gly Val Leu Leu Thr Asn Pro Ser Asn Pro Leu Gly Thr Ala Val Asp
        115                 120                 125

AGG GCG GTC CTG GAA GAC ATA CTA GAC TTC GCC GCC CGG AAG GAC ATC      432
Arg Ala Val Leu Glu Asp Ile Leu Asp Phe Ala Ala Arg Lys Asp Ile
130                 135                 140

CAC TCG ATA TCC GAC GAG ATC TAC TCG GGC TCG GTC TTC GCC TCT CCG      480
His Ser Ile Ser Asp Glu Ile Tyr Ser Gly Ser Val Phe Ala Ser Pro
145                 150                 155                 160

GAG TTC GAC AGC GTG GGG GAG ATC GTC GAG GCG CGG GGC TAC CGC ATC      528
Glu Phe Asp Ser Val Gly Glu Ile Val Glu Ala Arg Gly Tyr Arg Ile
                165                 170                 175

TGC GAG AGG GTA CAC ATT GTC TAC AGC CTC TCC AAG GAC TTA GGC CTC      576
Cys Glu Arg Val His Ile Val Tyr Ser Leu Ser Lys Asp Leu Gly Leu
                180                 185                 190

CCC GGT TTT AGG GTT GGG ACG ATC TAT TCA TAC AAC AAT AGG GTG GTG      624
Pro Gly Phe Arg Val Gly Thr Ile Tyr Ser Tyr Asn Asn Arg Val Val
                195                 200                 205

ACC ACG GCG AGG AGG ATG TCG AGC TTC ACA CTC GTG TCG TCG CAG ACT      672
Thr Thr Ala Arg Arg Met Ser Ser Phe Thr Leu Val Ser Ser Gln Thr
210                 215                 220

CAG AAG ACG CTG GCG TCG ATG CTG TCG GAC GAG GAG TTC ACA AAG TAC      720
Gln Lys Thr Leu Ala Ser Met Leu Ser Asp Glu Glu Phe Thr Lys Tyr
225                 230                 235                 240

TAC ATA AGG ACC AAC AGG GAG AGG CTG AAG AGG AGG TAC GAG TAC ATA      768
Tyr Ile Arg Thr Asn Arg Glu Arg Leu Lys Arg Arg Tyr Glu Tyr Ile
                245                 250                 255

ATC CAG GGG CTG GAG AGA GCA GGG ATT GAG TGC TTC CAA GGG AAT GCC      816
Ile Gln Gly Leu Glu Arg Ala Gly Ile Glu Cys Phe Gln Gly Asn Ala
                260                 265                 270

GGG CTG TTC TGC TGG ATG AAT CTG GGG CCA CTC CTG GAG GAG CAG ACG      864
Gly Leu Phe Cys Trp Met Asn Leu Gly Pro Leu Leu Glu Glu Gln Thr
                275                 280                 285

AGA GAA GGG GAG CTC AGC CTG TGG AAA CTG ATA TTG CAT GAG GTG AGG      912
Arg Glu Gly Glu Leu Ser Leu Trp Lys Leu Ile Leu His Glu Val Arg
290                 295                 300

CTC AAC ATA TCA CCA GGA TCT TCA TGC CAC TGC TCT GAG CCT GGC TGG      960
Leu Asn Ile Ser Pro Gly Ser Ser Cys His Cys Ser Glu Pro Gly Trp
305                 310                 315                 320

TTC CGT  GT                                                         968
Phe Arg (2) INFORMATION FOR SEQ ID NO:2:

(i) SEQUENCE CHARACTERISTICS:
        (A) LENGTH: 323 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

Phe Gln Asp Tyr His Gly Leu Lys Thr Phe Arg Lys Ala Met Ala Ser
1               5                  10                  15

Phe Met Glu Gln Ile Arg Gly Gly Lys Ala Lys Phe Asp Pro Asp Arg
                20                  25                  30

Ile Val Leu Ala Gly Gly Ala Thr Ala Ala Asn Gly Leu Leu Thr Phe
            35                  40                  45

Ile Leu Ala Asp Pro Gly Asp Ala Leu Leu Ile Pro Thr Pro Tyr Tyr
50                  55                  60
```

```
Pro Gly Phe Asp Arg Asp Leu Arg Trp Arg Thr Gly Val Asn Ile Val
65                  70                  75                  80

Pro Ile Arg Cys Asp Ser Ser Asn Gly Phe Gln Val Thr Leu Lys Ala
            85                  90                  95

Leu Glu Ala Ala Tyr Ala Lys Ala Glu Ala Ala Glu Met Lys Val Arg
        100                 105                 110

Gly Val Leu Leu Thr Asn Pro Ser Asn Pro Leu Gly Thr Ala Val Asp
        115                 120                 125

Arg Ala Val Leu Glu Asp Ile Leu Asp Phe Ala Ala Arg Lys Asp Ile
    130                 135                 140

His Ser Ile Ser Asp Glu Ile Tyr Ser Gly Ser Val Phe Ala Ser Pro
145                 150                 155                 160

Glu Phe Asp Ser Val Gly Glu Ile Val Glu Ala Arg Gly Tyr Arg Ile
                165                 170                 175

Cys Glu Arg Val His Ile Val Tyr Ser Leu Ser Lys Asp Leu Gly Leu
            180                 185                 190

Pro Gly Phe Arg Val Gly Thr Ile Tyr Ser Tyr Asn Asn Arg Val Val
        195                 200                 205

Thr Thr Ala Arg Arg Met Ser Ser Phe Thr Leu Val Ser Ser Gln Thr
210                 215                 220

Gln Lys Thr Leu Ala Ser Met Leu Ser Asp Glu Glu Phe Thr Lys Tyr
225                 230                 235                 240

Tyr Ile Arg Thr Asn Arg Glu Arg Leu Lys Arg Arg Tyr Glu Tyr Ile
                245                 250                 255

Ile Gln Gly Leu Glu Arg Ala Gly Ile Glu Cys Phe Gln Gly Asn Ala
            260                 265                 270

Gly Leu Phe Cys Trp Met Asn Leu Gly Pro Leu Leu Glu Glu Gln Thr
        275                 280                 285

Arg Glu Gly Glu Leu Ser Leu Trp Lys Leu Ile Leu His Glu Val Arg
    290                 295                 300

Leu Asn Ile Ser Pro Gly Ser Ser Cys His Cys Ser Glu Pro Gly Trp
305                 310                 315                 320

Phe Arg Val (2) INFORMATION FOR SEQ ID NO:3:

(i) SEQUENCE CHARACTERISTICS:
        (A) LENGTH: 961 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..102

(ix) FEATURE:
        (A) NAME/KEY: mat_peptide
        (B) LOCATION: 103..194

(ix) FEATURE:
        (A) NAME/KEY: CDS
        (B) LOCATION: 195..961

(xi) SEQUENCE DESCRIPTION: SEQ ID NO:3:

ACC CGA AAC CAG CCT GGC TCT ACT TCC GCA AAT GAG ATT CTC ATT TTC       48
Thr Arg Asn Gln Pro Gly Ser Thr Ser Ala Asn Glu Ile Leu Ile Phe
 1               5                  10                  15
```

```
TGC CTC GGC GAA CCT GGC GAC GCG TTC CTC GTT CCA ACT CCT TAC TAC        96
Cys Leu Gly Glu Pro Gly Asp Ala Phe Leu Val Pro Thr Pro Tyr Tyr
         20                  25                  30

CCT GGG TAAGTACTAT ACATATTCAC TCCTATATAT ATTAATATGC TCTTCTTGTA        152
Pro Gly

CGTTTTTCCC ATGTATACTA AATATGCTGT TTAACTTGCA GG TTT GAT AGG GAT        206
                                              Phe Asp Arg Asp
                                               1

CTC AAA TGG CGG ACT GGT GCG GAG ATC ATA CCG ATC CAC TGC TCG AGC       254
Leu Lys Trp Arg Thr Gly Ala Glu Ile Ile Pro Ile His Cys Ser Ser
 5              10                  15                  20

TCG AGC GGG TTT CGG ATC ACC AAA CCC GCG CTC GAA GAG GCT TAT CAT       302
Ser Ser Gly Phe Arg Ile Thr Lys Pro Ala Leu Glu Glu Ala Tyr His
             25                  30                  35

CAA GCT CAG CAG CAG AAG CTA AGA GTG AAG GGA GTG TTG GTC ACC AAC       350
Gln Ala Gln Gln Gln Lys Leu Arg Val Lys Gly Val Leu Val Thr Asn
         40                  45                  50

CCC TCG AAC CCT TTG GGC ACC ACA TTG TGC ACC CGT GAG CTA GAA ACC       398
Pro Ser Asn Pro Leu Gly Thr Thr Leu Val His Arg Glu Leu Glu Thr
     55                  60                  65

CTA ATC GAC TTC ATT GTG GCC AAA GGC ATC CAT CTG ATC AGC GAT GAG       446
Leu Ile Asp Phe Ile Val Ala Lys Gly Ile His Leu Ile Ser Asp Glu
 70                  75                  80

ATA TAC TCC GGC ACC AAC TGC GAC TCT CCG GGT TTC ATA AGT GTC GCT       494
Ile Tyr Ser Gly Thr Asn Cys Asp Ser Pro Gly Phe Ile Ser Val Ala
 85                  90                  95                 100

GAG GCG ATA ACC GAA CGA GGC GAA GAG GTG GCG GAC CGT GTA CAC ATC       542
Glu Ala Ile Thr Glu Arg Gly Glu Glu Val Ala Asp Arg Val His Ile
             105                 110                 115

GTG TAT AGC TTA TCG AAG GAC CTC GGG CTA CCA GGC TTT CGC GTC GGT       590
Val Tyr Ser Leu Ser Lys Asp Leu Gly Leu Pro Gly Phe Arg Val Gly
         120                 125                 130

GCG ATA CAC TCC CAA AAT GAG GCG GTG GTC TCC ACG GCG ACC AAG ATG       638
Ala Ile His Ser Gln Asn Glu Ala Val Val Ser Thr Ala Thr Lys Met
         135                 140                 145

TCG AGC TTT GGG CTC ATC TCC TCT CAA ACT CAG TAC TTC TTG TCC TTG       686
Ser Ser Phe Gly Leu Ile Ser Ser Gln Thr Gln Tyr Phe Leu Ser Leu
     150                 155                 160

TTG CTC TCC GAC AAG GAG TTC ACA GCG AAC TAC ATA GCG GAG AAC AAG       734
Leu Leu Ser Asp Lys Glu Phe Thr Ala Asn Tyr Ile Ala Glu Asn Lys
165                 170                 175                 180

AAG CGG CTT AGA GAG CGG CAA AAG CGG CTC ACC GAA GCG CTG CGG ACG       782
Lys Arg Leu Arg Glu Arg Gln Lys Arg Leu Thr Glu Ala Leu Arg Thr
             185                 190                 195

ATC GGT ATA AAC TGT TTG GAG AGC AAT GCA GGG TTG TTT TGT TGG GTG       830
Ile Gly Ile Asn Cys Leu Glu Ser Asn Ala Gly Leu Phe Cys Trp Val
             200                 205                 210

GAC ATG AGG CAC TTA CTT AAG TCT AAG ACA CCT GAA GGA GAG ATG GAG       878
Asp Met Arg His Leu Leu Lys Ser Lys Thr Pro Glu Gly Glu Met Glu
         215                 220                 225

CTG TGG AAA AGG ATA GTG CAT GAT GTG GGA CTA AAC ATT TCT CCG GGC       926
Leu Trp Lys Arg Ile Val His Asp Val Gly Leu Asn Ile Ser Pro Gly
     230                 235                 240

TCT TCG TCC ACT CAA CGA CCT GGC TGG TTC CGC GT                        961
Ser Ser Ser Thr Gln Arg Pro Gly Trp Phe Arg
245                 250                 255

(2) INFORMATION FOR SEQ ID NO:4:
```

(i) SEQUENCE CHARACTERISTICS:
            (A) LENGTH: 289 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:4:

Thr Arg Asn Gln Pro Gly Ser Thr Ser Ala Asn Glu Ile Leu Ile Phe
1               5                   10                  15

Cys Leu Gly Glu Pro Gly Asp Ala Phe Leu Val Pro Thr Pro Tyr Tyr
            20                  25                  30

Pro Gly Phe Asp Arg Asp Leu Lys Trp Arg Thr Gly Ala Glu Ile Ile
        35                  40                  45

Pro Ile His Cys Ser Ser Ser Gly Phe Arg Ile Thr Lys Pro Ala
50                  55                  60

Leu Glu Glu Ala Tyr His Gln Ala Gln Gln Lys Leu Arg Val Lys
65                  70                  75                  80

Gly Val Leu Val Thr Asn Pro Ser Asn Pro Leu Gly Thr Thr Leu Val
            85                  90                  95

His Arg Glu Leu Glu Thr Leu Ile Asp Phe Ile Val Ala Lys Gly Ile
            100                 105                 110

His Leu Ile Ser Asp Glu Ile Tyr Ser Gly Thr Asn Cys Asp Ser Pro
            115                 120                 125

Gly Phe Ile Ser Val Ala Glu Ala Ile Thr Glu Arg Gly Glu Glu Val
        130                 135                 140

Ala Asp Arg Val His Ile Val Tyr Ser Leu Ser Lys Asp Leu Gly Leu
145                 150                 155                 160

Pro Gly Phe Arg Val Gly Ala Ile His Ser Gln Asn Glu Ala Val Val
            165                 170                 175

Ser Thr Ala Thr Lys Met Ser Ser Phe Gly Leu Ile Ser Ser Gln Thr
            180                 185                 190

Gln Tyr Phe Leu Ser Leu Leu Leu Ser Asp Lys Glu Phe Thr Ala Asn
        195                 200                 205

Tyr Ile Ala Glu Asn Lys Lys Arg Leu Arg Glu Arg Gln Lys Arg Leu
210                 215                 220

Thr Glu Ala Leu Arg Thr Ile Gly Ile Asn Cys Leu Glu Ser Asn Ala
225                 230                 235                 240

Gly Leu Phe Cys Trp Val Asp Met Arg His Leu Leu Lys Ser Lys Thr
            245                 250                 255

Pro Glu Gly Glu Met Glu Leu Trp Lys Arg Ile Val His Asp Val Gly
            260                 265                 270

Leu Asn Ile Ser Pro Gly Ser Ser Thr Gln Arg Pro Gly Trp Phe
            275                 280                 285

Arg (2) INFORMATION FOR SEQ ID NO:5:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:5:

TAYTTYGAYG GNTGGAARGC                                              20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

TCRTCCATRT TNGCRAARCA                                              20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

CARATGGGNY TNGCNGARAA                                              20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

GCRAARCANA CNCYRAACCA                                              20

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

ACNCKRAACC ANCCNGGNTC                                              20

(2) INFORMATION FOR SEQ ID NO:10:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

TTYCARGAYT AYCAYGG                                                 17

I claim:

1. An isolated nucleotide sequence encoding an ACC synthase enzyme comprising the sequence of amino acids identified by SEQ ID NO:2.

2. The isolated nucleotide sequence of claim 1 wherein said isolated nucleotide sequence is identified by SEQ ID NO:1.

3. An isolated nucleotide sequence encoding an ACC synthase enzyme comprising the sequence of amino acids identified by SEQ ID NO:4.

4. The isolated nucleotide sequence of claim 3 wherein said isolated nucleotide sequence is identified by SEQ ID NO:3.

5. An isolated nucleotide sequence which is of sufficient length to regulate the level of ACC synthase gene expression and which hybridizes under high stringency wash conditions with SEQ ID NO:1, wherein said high stringency wash conditions are selected from the group consisting of: (i) 0.1× SSC/0.1% SDS at about 68° C. for at least about 20 minutes, and (ii) 0.2× SSC/0.1% SDS at about 68° C. for about one hour.

6. An isolated nucleotide sequence which is of sufficient length to regulate the level of ACC synthase gene expression and which hybridizes under high stringency wash conditions with SEQ ID NO:3, wherein said high stringency wash conditions are selected from the group consisting of: (i) 0.1× SSC/0.1% SDS at about 68° C. for at least about 20 minutes, and (ii) 0.2× SSC/0.1% SDS at about 68° C. for about one hour.

7. An isolated ACC synthase nucleotide sequence which hybridizes under high stringency wash conditions with SEQ ID NO:1, wherein said high stringency wash conditions are selected from the group consisting of: (i) 0.1× SSC/0.1% SDS at about 68° C. for at least about 20 minutes, (ii) 0.2× SSC/0.1% SDS at about 55° C. for about one hour, (iii) 0.2× SSC/0.1% SDS at about 62° C. for about one hour, and (iv) 0.2× SSC/0.1% SDS at about 68° C. for about one hour.

8. An isolated ACC synthase nucleotide sequence which hybridizes under high stringency wash conditions with SEQ ID NO:3, wherein said high stringency wash conditions are selected from the group consisting of: (i) 0.1× SSC/0.1% SDS at about 68° C. for at least about 20 minutes, (ii) 0.2× SSC/0.1% SDS at about 55° C. for about one hour, (iii) 0.2× SSC/0.1% SDS at about 62° C. for about one hour, and (iv) 0.2× SSC/0.1% SDS at about 68° C. for about one hour.

9. The isolated nucleotide sequence of any one of claims 5, 6, 7 and 8, wherein said isolated nucleotide sequence is obtained from a cell or tissue of a pineapple plant.

10. The isolated nucleotide sequence of any one of claims 5, 6, 7 and 8, wherein said isolated nucleotide sequence is obtained from a cell or tissue of a D leaf of a pineapple plant.

11. The isolated nucleotide sequence of any one of claims 5, 6, 7 and 8, wherein said isolated nucleotide sequence is obtained from a cell or tissue of a basal white portion of a D leaf of a pineapple plant.

12. The isolated nucleotide sequence of any one of claims 5, 6, 7 and 8, wherein said isolated nucleotide sequence is obtained from a cell or tissue of a stem apex of a pineapple plant.

13. A vector comprising at least one copy of the nucleotide sequence of claim 1 or claim 2.

14. A vector comprising at least one copy of the nucleotide sequence claim 3 or claim 4.

15. The vector of claim 13 wherein said nucleotide sequence is under control of one or more regulatory nucleotide sequences.

16. The vector of claim 14 wherein said nucleotide sequence is under control of one or more regulatory nucleotide sequences.

17. A vector comprising at least one copy of the nucleotide sequence of any one of claims 5, 6, 7 and 8.

18. The vector of claim 17 wherein said nucleotide sequence is under control of one or more regulatory nucleotide sequences.

19. A method of producing a transgenic pineapple plant, including the steps of introducing into a pineapple plant, plant part or plant cell a vector comprising the nucleotide sequence of claim 1 or claim 2 wherein said nucleotide sequence is operably linked, in the sense orientation, to one or more regulatory nucleotide sequences, and growing said plant, plant part or plant cell to produce the transgenic pineapple plant.

20. A method of producing a transgenic pineapple plant, including the steps of introducing into a pineapple plant, plant part or plant cell a vector comprising the nucleotide sequence of claim 3 or claim 4 wherein said nucleotide sequence is operably linked, in the sense orientation, to one or more regulatory nucleotide sequences, and growing said plant, plant part or plant cell to produce the transgenic pineapple plant.

21. A method of producing a transgenic pineapple plant, including the steps of introducing into a pineapple plant, plant part or plant cell a vector comprising the nucleotide sequence of claim 1 or claim 2 wherein said nucleotide sequence is operably linked, in the antisense orientation, to one or more regulatory nucleotide sequences, and growing said plant, plant part or plant cell to produce the transgenic pineapple plant.

22. A method of producing a transgenic pineapple plant, including the steps of introducing into a pineapple plant, plant part or plant cell a vector comprising the nucleotide sequence of claim 3 or claim 4 wherein said nucleotide sequence is operably linked, in the antisense orientation, to one or more regulatory nucleotide sequences, and growing said plant, plant part or plant cell to produce the transgenic pineapple plant.

23. A method of producing a transgenic pineapple plant including the steps of introducing into a pineapple plant, plant part or plant cell a vector comprising the nucleotide sequence of any one of claims 5, 6, 7 and 8, wherein said nucleotide sequence is operably linked, in the sense orientation, to one or more regulatory nucleotide sequences, and growing said plant, plant part or plant cell to produce the transgenic pineapple plant.

24. A method of producing a transgenic pineapple plant, including the steps of introducing into a pineapple plant, plant part or plant cell a vector comprising the nucleotide sequence of any one of claims 5, 6, 7 and 8, wherein said nucleotide sequence is operably linked, in the antisense orientation, to one or more regulatory nucleotide sequences, and growing said plant, plant part or plant cell to produce the transgenic pineapple plant.

25. A transgenic pineapple plant transformed with a vector comprising the nucleotide sequence of claim 1 or claim 2 wherein said nucleotide sequence is operably linked, in the sense orientation, to one or more regulatory nucleotide sequences.

26. A transgenic pineapple plant transformed with a comprising the nucleotide sequence of claim 3 or claim 4 wherein said nucleotide sequence is operably linked, in the sense orientation, to one or more regulatory nucleotide sequences.

27. A transgenic pineapple plant transformed with a vector comprising the nucleotide sequence of claim 1 or claim 2 wherein said nucleotide sequence is operably linked, in the antisense orientation, to one or more regulatory nucleotide sequences.

28. A transgenic pineapple plant transformed with a vector comprising the nucleotide sequence of claim 3 for claim 4 wherein said nucleotide sequence is operably linked, in the antisense orientation, to one or more regulatory nucleotide sequences.

29. A transgenic pineapple plant transformed with a vector comprising the nucleotide sequence of any one of claims 5, 6, 7 and 8, wherein said nucleotide sequence is operably linked, in the sense orientation, to one or more regulatory nucleotide sequences.

30. A transgenic pineapple plant transformed with a vector comprising the nucleotide sequence of any one of claims 5, 6, 7 and 8, wherein said nucleotide sequence is operably linked, in the antisense orientation, to one or more regulatory nucleotide sequences.

31. A pineapple fruit, fruit part or fruit cell produced from the transgenic pineapple plant of claim 25.

32. A pineapple fruit, fruit part or fruit cell produced from the transgenic pineapple plant of claim 26.

33. A pineapple fruit, fruit part or fruit cell produced from the transgenic pineapple plant of claim 27.

34. A pineapple fruit, fruit part or fruit cell produced from the transgenic pineapple plant of claim 28.

35. A pineapple fruit, fruit part or fruit cell produced from the transgenic pineapple plant of claim 29.

36. A pineapple fruit, fruit part or fruit cell produced from the transgenic pineapple plant of claim 30.

* * * * *